(12) United States Patent
Cho et al.

(10) Patent No.: US 9,343,319 B2
(45) Date of Patent: May 17, 2016

(54) INSPECTION METHOD AND METHOD OF MANUFACTURING SEMICONDUCTOR DEVICE

(71) Applicant: Renesas Electronics Corporation, Kawasaki-shi, Kanagawa (JP)

(72) Inventors: Shien Cho, Kanagawa (JP); Takahiro Hara, Ibaraki (JP); Kenichi Ito, Ibaraki (JP)

(73) Assignee: Renesas Electronics Corporation, Kanagawa (JP)

( * ) Notice: Subject to any disclaimer, the term of this patent is extended or adjusted under 35 U.S.C. 154(b) by 0 days.

(21) Appl. No.: 14/531,462

(22) Filed: Nov. 3, 2014

(65) Prior Publication Data

US 2015/0125969 A1 May 7, 2015

(30) Foreign Application Priority Data

Nov. 6, 2013 (JP) .................................. 2013-230363

(51) Int. Cl.
*H01L 21/66* (2006.01)
*H01L 21/285* (2006.01)
*G01N 25/48* (2006.01)
*G01N 5/04* (2006.01)
*H01L 21/28* (2006.01)

(52) U.S. Cl.
CPC ............ *H01L 21/28556* (2013.01); *G01N 5/04* (2013.01); *G01N 25/4846* (2013.01); *H01L 22/12* (2013.01); *H01L 21/28202* (2013.01)

(58) Field of Classification Search
CPC ................ H01L 22/10; H01L 21/0214; H01L 21/02164; H01L 21/20835; H01L 21/28556; G01N 25/72
USPC .......................................................... 438/14
See application file for complete search history.

(56) References Cited

U.S. PATENT DOCUMENTS 6,187,693 B1 * 2/2001 Koyanagi ...................... 438/785
2004/0084736 A1 * 5/2004 Harada .......................... 257/410

OTHER PUBLICATIONS

SCAS News 2004-I, pp. 11-14.
Hideo Ota, et al., "Scanning Surface Inspection System with Defect Review SEM and Analysis System Solution", Hitachi Review, 2006, pp. 65-68, vol. 88, No. 3.
Mari Nozoe et al., "Inspection-Analysis Solutions for High-Quality and High-Efficiency Semiconductor Device Manufacturing", Hitachi Review, 2004, pp. 465 to 470, vol. 86, No. 7.

* cited by examiner

*Primary Examiner* — Reema Patel
*Assistant Examiner* — Syed Gheyas
(74) *Attorney, Agent, or Firm* — Sughrue Mion, PLLC

(57) ABSTRACT

First, a product to be inspected is prepared. The product to be inspected includes a substrate and a first film formed on the substrate. TDS is performed while the temperature of the product to be inspected is raised to 1,000° C. or higher, and the quality of the product to be inspected is determined by checking for the presence or absence of a peak at 1,000° C. or higher. Meanwhile, the substrate is, for example, a semiconductor substrate such as a silicon substrate. In addition, the rate of temperature rise is, for example, equal to or higher than 40° C./min and equal to or lower than 80° C./min. The upper limit of the temperature of TDS is, for example, 1,300° C.

19 Claims, 9 Drawing Sheets

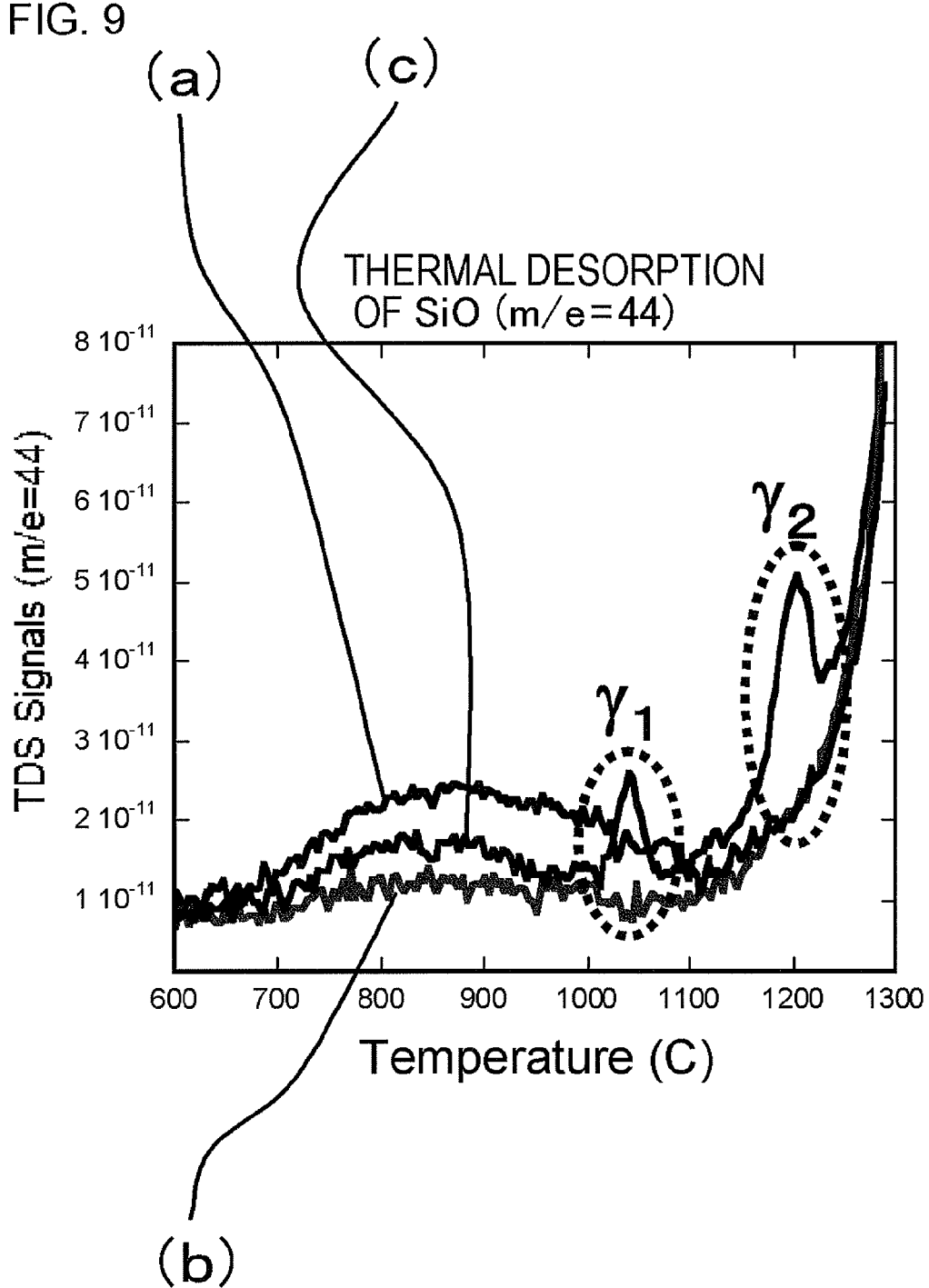

INSPECTION METHOD AND METHOD OF MANUFACTURING SEMICONDUCTOR DEVICE

This application is based on Japanese patent application No. 2013-230363, the content of which is incorporated hereinto by reference.

BACKGROUND

1. Technical Field

The present invention relates to an inspection method and a method of manufacturing a semiconductor device, and to a technique applicable to, for example, a method of reducing the percent defective of a semiconductor device.

2. Related Art

In order to reduce the percent defective of a semiconductor device, it is important to guarantee the quality of a film of the semiconductor device. Particularly, the analysis of the surface of the film is essential. For example, a method (for example, SCAS News 2004-I pp 11-14) of analyzing components of elements (for example, films) constituting a semiconductor device, a method (for example, Hitachi Review, Vol. 88 No. 3 pp: 65-68 (2006) and Hitachi Review, Vol. 86, No. 7, pp: 465 to 470 (2004)) of measuring the surface shape of a film, and the like are used in this analysis.

When a film is formed on a substrate, film-forming conditions at the moment of terminating film formation are different from film-forming conditions when the film formation is continuing. In addition, since the surface of the film comes into contact with the atmosphere, the composition of the surface of the film is often different from the internal composition of the film. The inventors have found that a surface layer like a "cover" that restricts the infiltration of impurities into a film is present on the surface of the film. Based on such new knowledge, the inventors consider that since the composition of the surface of a film formed on a substrate influences "sealing performance" of a "cover" of the surface, the composition may greatly influence the percent defective of a semiconductor device. However, although there is a method of checking the shape of a film surface or an adsorbate of the surface, it has been difficult to check whether the composition of the film surface is in a normal state.

Other problems and novel features will be made clearer from the description and the accompanying drawings of the present specification.

SUMMARY

In one embodiment, thermal desorption spectrometry (TDS) is performed on a product to be inspected including a substrate and a first film formed over the substrate while the temperature is raised to 1,000° C. or higher. The quality of the product to be inspected is determined by checking for the presence or absence of a peak at 1,000° C. or higher.

According to the embodiment, it is possible to easily check whether the composition of the surface of a film is in a normal state.

BRIEF DESCRIPTION OF THE DRAWINGS

The above and other objects, advantages and features of the present invention will be more apparent from the following description of certain preferred embodiments taken in conjunction with the accompanying drawings, in which:

FIG. 9 is a diagram illustrating results of TDS in a third embodiment.

DETAILED DESCRIPTION

Figure 1:
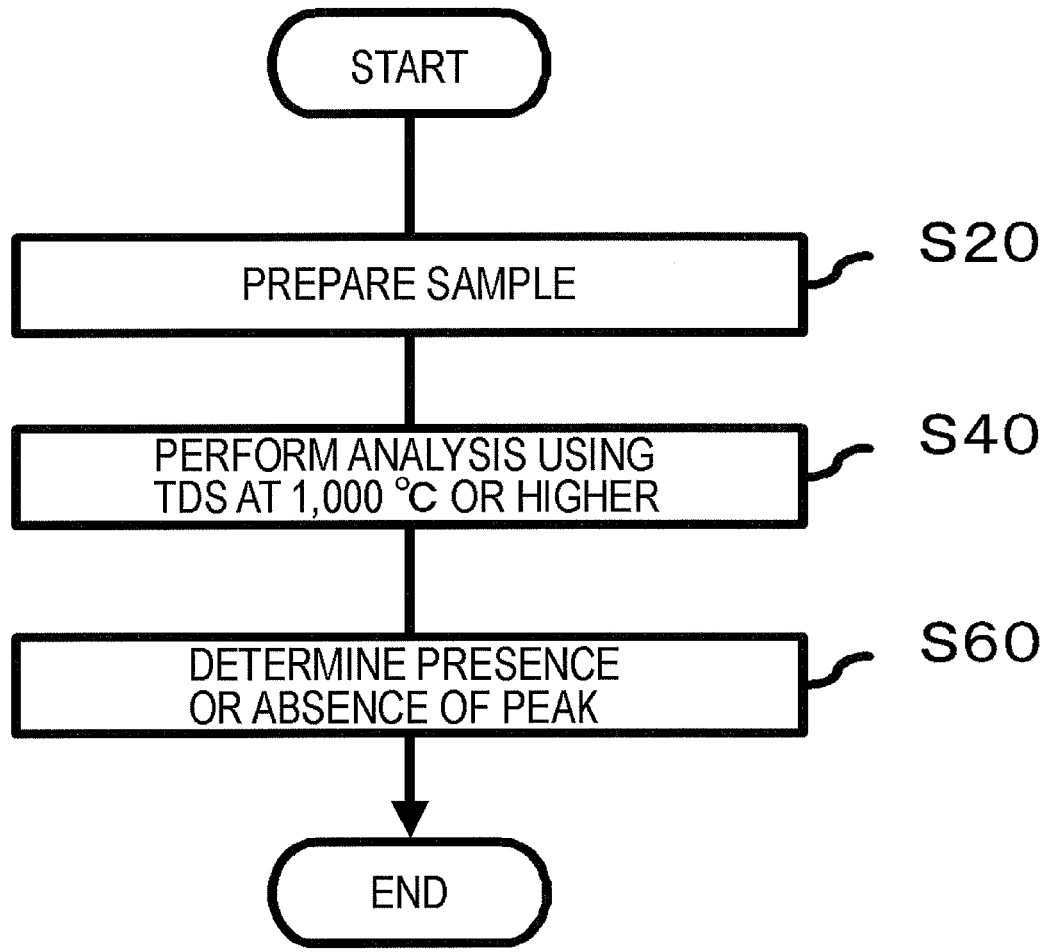
FIG. 1 is a flow diagram illustrating an inspection method according to a first embodiment.

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Hereinafter, embodiments of the present invention will be described with reference to the accompanying drawings. In all the drawings, like elements are referenced by like reference numerals and descriptions thereof will not be repeated.

First Embodiment

Figure 2:
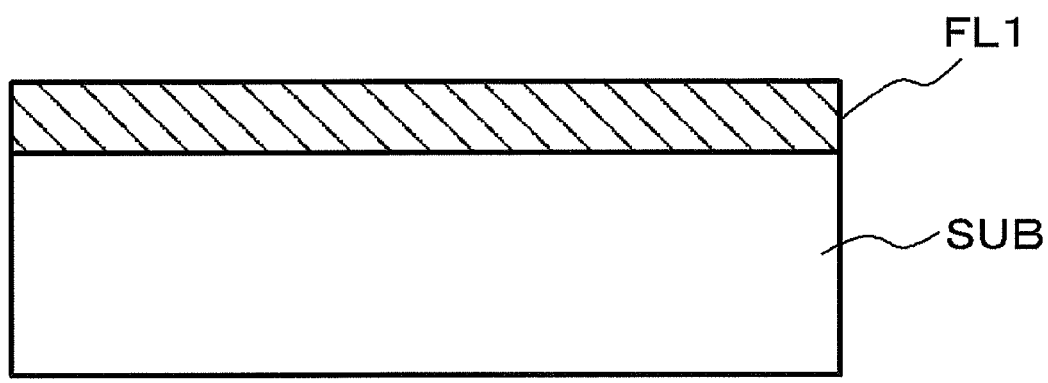
FIG. 2 is a cross-sectional view illustrating a configuration of a product to be inspected in the inspection method shown in FIG. 1.

FIG. 1 is a flow diagram illustrating an inspection method according to a first embodiment. FIG. 2 is a cross-sectional view illustrating a configuration of a product to be inspected in the inspection method shown in FIG. 1. The inspection method according to the present embodiment is performed using thermal desorption spectrometry (TDS), and includes the following steps. First, a product to be inspected is prepared (step S20). The product to be inspected includes a substrate SUB and a first film FL1 formed on the substrate SUB. TDS is performed while the temperature of the product to be inspected is raised to 1,000° C. or higher (step S40), and the quality of the product to be inspected is determined by checking for the presence or absence of a peak at 1,000° C. or higher (step S60). Meanwhile, the substrate SUB is, for example, a semiconductor substrate such as a silicon substrate. In addition, the rate of temperature rise is, for example, equal to or higher than 0.1° C./min and equal to or lower than 120° C./min. The upper limit of the temperature of TDS is, for example, 1,300° C.

In the example shown in FIG. 2, the first film FL1 is provided directly on the substrate SUB. However, another film may be present between the substrate SUB and the first film FL1, and an underlayer film may be provided in order to reproduce the structure of a device insofar as possible. The first film FL1 is, for example, a silicon-containing film such as a polysilicon film, an epitaxial silicon film, or a film containing silicon oxide as a main component. However, the first film FL1 may be another film. In addition, the first film FL1 is formed using, for example, a CVD method. In this case, particularly, the composition of the surface of the first film FL1 has a tendency to be different from the internal composition of the first film FL1. When the first film FL1 is a silicon-containing film, a silane-based gas, for example, is used as a source gas of CVD. The mass (M/e) of the object to be detected in TDS includes at least one of 2 ($H_2$), 17 (HO), 18 ($H_2O$), 44 (SiO), and 45 (SiO).

TDS is generally performed at a temperature of lower than 1,000° C. On the other hand, in the present embodiment, the temperature of the product to be inspected is raised to 1,000° C. or higher. Thereby, elements which are bound to the first film FL1 on the surface of the first film FL1 are desorbed from the first film FL1. Thereby, a desorption peak caused by these elements is observed at 1,000° C. or higher. Therefore, it is possible to determine whether the surface state of the first film FL1 is normal, on the basis of the presence or absence of this peak. For example, when a peak is observed at 1,000° C. or higher in a normal product to be inspected, a product to be inspected in which such a peak is not able to be detected is determined to be a defective product. On the other hand, when a peak is not observed at 1,000° C. or higher in a normal product to be inspected, a product to be inspected in which such a peak is detected is determined to be a defective product. It is possible to determine whether a process of forming the first film FL1 is normal, on the basis of the inspection results. When the process is not normal, the percent defective of an element can be reduced by optimizing the process.

Figure 3:
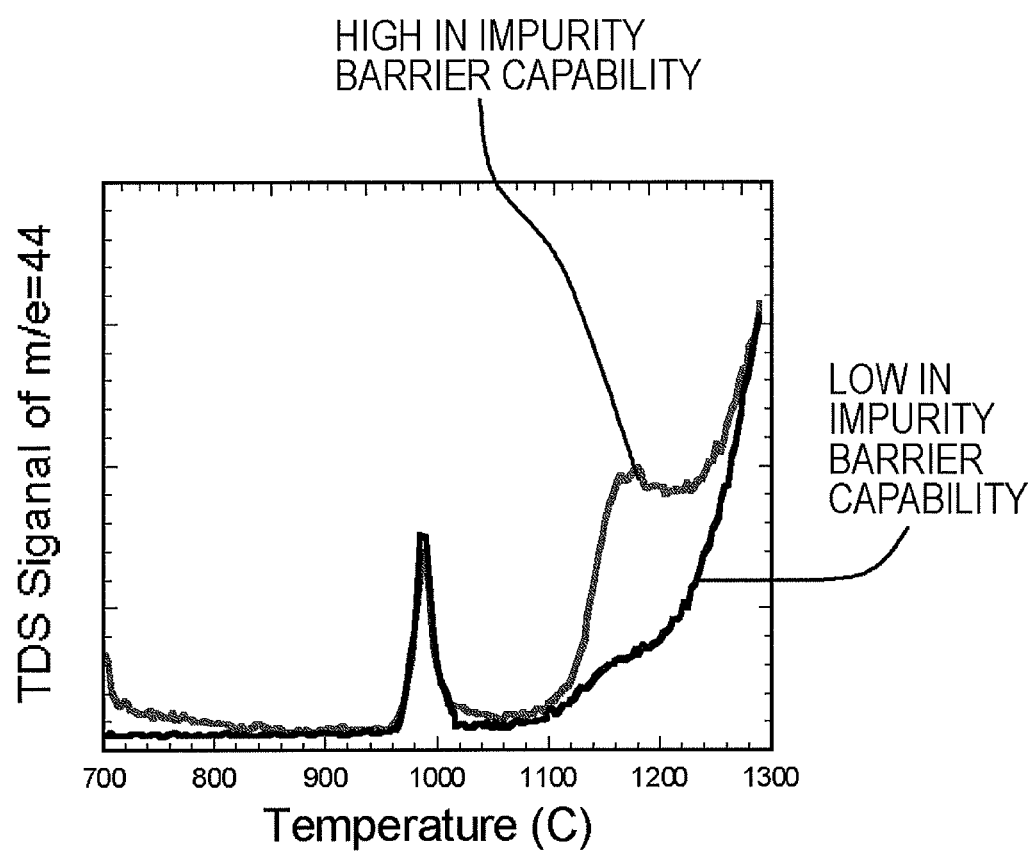
FIG. 3 is a diagram illustrating results of TDS for a substance having a mass of 44 when a first film FL1 is a polysilicon film.

FIG. 3 is a diagram illustrating results of TDS for a substance (that is, SiO) having a mass of 44 when the first film FL1 is a polysilicon film. For example, when the first film FL1 is a silicon-containing film, in TDS, a peak caused by SiO appears in a range of equal to or higher than 1,000° C. and equal to or lower than 1,200° C., particularly, a range of equal to or higher than 1,100° C. and equal to or lower than 1,200° C. In addition, when such a peak is observed, the impurity barrier capability of the first film FL1 is greater than in the case where a peak is not observed. Therefore, in TDS, it is possible to determine whether the first film FL1 is normal by determining whether a peak appears in a range of equal to or higher than 1,000° C. and equal to or lower than 1,200° C., particularly, a range of equal to or higher than 1,100° C. and equal to or lower than 1,200° C. For example, when the first film FL1 is used as a gate electrode and a peak appears in a range of equal to or higher than 1,000° C. and equal to or lower than 1,200° C., particularly, a range of equal to or higher than 1,100° C. and equal to or lower than 1,200° C., the first film FL1 is determined to be normal.

Meanwhile, in TDS, when a peak caused by SiO appears in a range of equal to or higher than 1,000° C. and equal to or lower than 1,200° C., particularly, a range of equal to or higher than 1,100° C. and equal to or lower than 1,200° C., it is considered that an extremely thin layer having gas barrier capability (for example, hydrogen barrier capability) is formed on the surface of the first film FL1. When the first film FL1 is a silicon-containing film, it is considered that this layer is a SiON layer of which the surface terminates with H, $H_2O$, or OH. It is considered that this layer is decomposed by heat and components after the decomposition are detected by TDS.

As stated above, according to the present embodiment, the temperature of the product to be inspected is raised to 1,000° C. or higher in TDS. It is possible to determine whether the surface state of the first film FL1 is normal, on the basis of the presence or absence of a peak at 1,000° C. or higher.

Meanwhile, when the inspection method shown in the present embodiment is applied to the method of manufacturing a semiconductor device, the results are, for example, as follows. First, the method of manufacturing a semiconductor device includes a first film forming process of forming the first film FL1 on substrates SUB. The first film forming process is performed on a first one of the substrates SUB and then TDS is performed on the first substrate SUB while a processing temperature is raised to 1,000° C. or higher, and the presence or absence of a peak at 1,000° C. or higher is checked for. The quality of a laminated film of the first film and a second film is determined according to the results. When the height of the peak satisfies a reference, the first film forming process is performed on at least a second one of the substrates SUB. Thereby, it is possible to prevent the semiconductor device from becoming defective due to the surface state of the first film. Meanwhile, the first substrate SUB is treated as a sample, and the second substrate SUB is treated as a product.

Second Embodiment

Figure 4A:
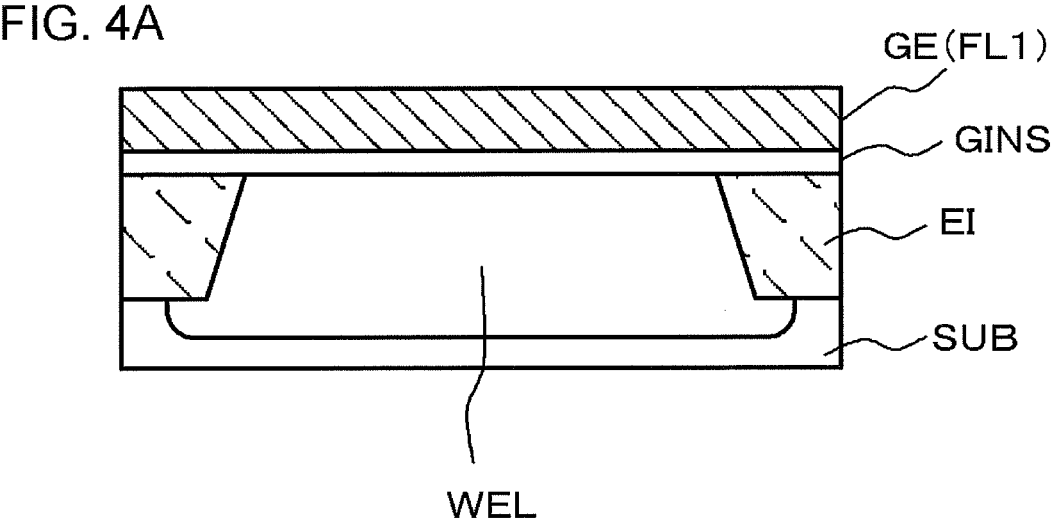
FIGS. 4A and 4B are cross-sectional views illustrating a method of manufacturing a semiconductor device according to a second embodiment.
Figure 4B:
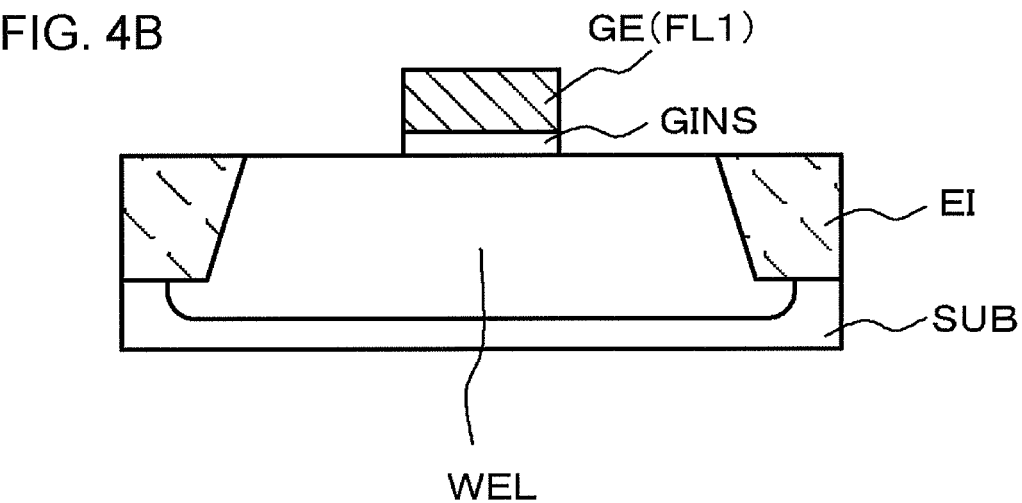
Figure 5:
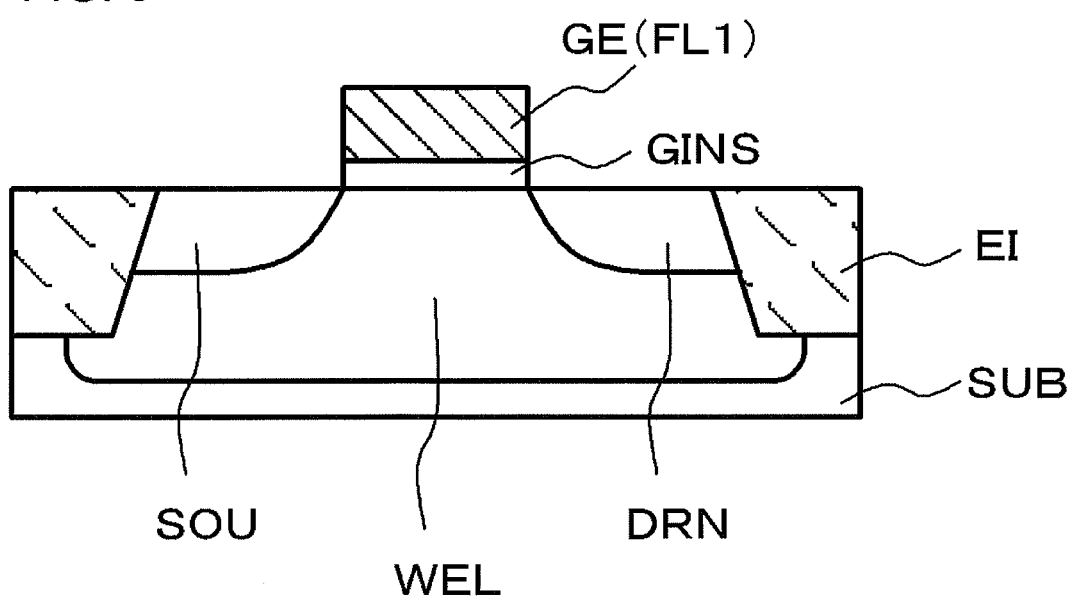
FIG. 5 is a cross-sectional view illustrating a method of manufacturing the semiconductor device according to the second embodiment.

FIGS. 4A and 4B and FIG. 5 are cross-sectional views illustrating a method of manufacturing a semiconductor device according to a second embodiment. First, as shown in FIG. 4A, an element isolation film EI and a well WEL are formed in the substrate SUB. The element isolation film EI is formed using, for example, an STI method, but may be formed using a LOCOS method. In addition, the well WEL is a first conductivity type impurity region, and is formed using an ion implantation method. The well WEL may be formed ahead of the element isolation film EI, and may be formed after the element isolation film EI.

Next, a gate insulating film GINS (second film) is formed on the substrate SUB and on the element isolation film EI (second film forming process). The gate insulating film GINS is, for example, a silicon oxide film or a silicon oxynitride film. The thickness of the gate insulating film GINS is equal to or greater than 1 nm and equal to or less than 200 nm, for example, equal to or greater than 5 nm and equal to or less than 15 nm. In the example shown in the drawing, the gate insulating film GINS is formed using a deposition method (for example, CVD method), and thus is also formed on the element isolation film EI. In this case, the gate insulating film GINS is a film (for example, TEOS film) called a high temperature oxide (HTO) film, or a film obtained by processing the HTO using nitrogen plasma (or $N_2O$ annealing or NO annealing). However, the gate insulating film GINS may be formed using a thermal oxidation method. In this case, the gate insulating film GINS is formed in a region of the surface of the substrate SUB on which the element isolation film EI is not formed.

Next, a gate electrode GE as the first film FL1 is formed on the gate insulating film GINS (first film forming process). The gate electrode GE is, for example, a polysilicon film, and is formed using a CVD method such as a plasma CVD method. The film thickness of the gate electrode GE is, for example, equal to or greater than 50 nm and equal to or less than 1,000 nm.

Next, the laminated film of the gate electrode GE and the gate insulating film GINS is selectively removed. Such a process is performed, for example, as follows. First, a resist pattern is formed on the gate electrode GE. Next, the gate electrode GE and the gate insulating film GINS are dry-etched using this resist pattern as a mask. Thereafter, the resist pattern is removed.

Next, as shown in FIG. 5, a second conductivity type impurity is ion-implanted into the substrate SUB, using the gate electrode GE and the element isolation film EI as a mask. Thereby, a source SOU and a drain DRN are formed in the well WEL. The impurity is activated by performing heat treatment in for example, a nitrogen atmosphere. A heat treatment temperature in this case is, for example, equal to or higher than 900° C. and equal to or lower than 1,100° C.

Meanwhile, although not shown in FIG. 5, a sidewall may be formed at the lateral side of the gate electrode GE. In this case, a low-concentration diffusion region (for example, LDD region) is formed in a region of the well WEL which is located below the sidewall.

Meanwhile, the gate insulating film GINS, the gate electrode GE, the source SOU, and the drain DRN are used as for example, a MOS transistor or a MOS capacitor. In addition, the gate insulating film GINS, the gate electrode GE, the source SOU, and the drain DRN may be used as a portion of a nonvolatile memory. In this case, the gate insulating film GINS functions as a tunnel insulating film of the nonvolatile memory. Other components of the nonvolatile memory are also formed.

Thereafter, at least one interconnect layer is formed. Thereafter, heat treatment is performed in a hydrogen atmosphere. The heat treatment temperature in this case is, for example, equal to or higher than 350° C. and equal to or lower than 450° C.

Figure 6:
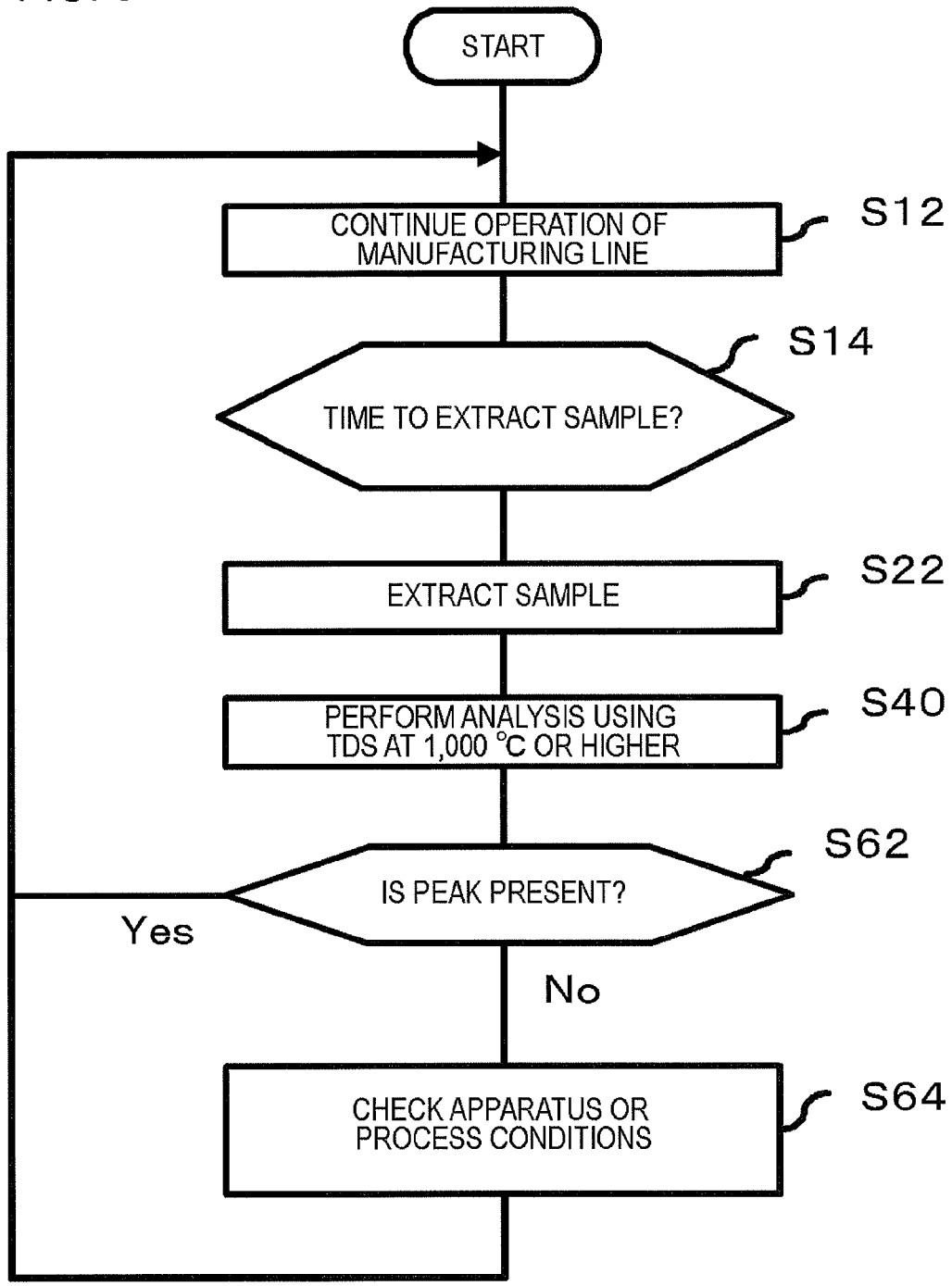
FIG. 6 is a diagram illustrating an example of a flow diagram when the inspection method shown in the first embodiment is applied in the method of manufacturing the semiconductor device shown in FIGS. 4A and 4B and FIG. 5.

FIG. 6 shows an example of a flow diagram when the inspection method shown in the first embodiment is applied in the method of manufacturing a semiconductor device shown in FIGS. 4A and 4B and FIG. 5. In the process shown in the drawing, whether the gate electrode GE (first film) is normally formed is inspected by periodically extracting a sample (first substrate). When the extracted sample is normal, the processes shown in FIGS. 4A and 4B and FIG. 5 are performed on the predetermined number of substrates SUB (second substrates). Thereafter, the flow returns to a process of extracting the sample. On the other hand, when the extracted sample is defective, a manufacturing line is stopped, a manufacturing apparatus or process conditions are checked, and then the operation of the manufacturing line is restarted.

The substrate SUB serving as a sample is the substrate SUB in a state shown in FIG. 4A, that is, a substrate which is extracted after the gate insulating film GINS and the gate electrode GE are formed on the substrate SUB and before the gate electrode GE and the gate insulating film GINS are patterned. For this reason, the area of the gate electrode GE becomes larger than the area thereof after the patterning, and thus the amount of gas desorbed from the gate electrode GE increases. For this reason, the accuracy of inspection increases. Hereinafter, a detailed description will be given.

First, the operation of the manufacturing line is continued, and the processes shown in FIGS. 4A and 4B and FIG. 5 are performed on each of a plurality of substrates SUB (step S12). When the time comes to extract a sample (step S14: Yes), the substrate SUB (first substrate) serving as a sample is extracted (step S22). Next, the extracted substrate SUB is heated to 1,000° C. or higher, and is analyzed using TDS (step S40). The mass of a substance to be inspected in this case is, for example, 44 (that is, SiO).

In the results of TDS, when a peak is present in a range of equal to or higher than 1,000° C. and equal to or lower than 1,200° C., particularly, a range of equal to or higher than 1,100° C. and equal to or lower than 1,200° C. (step S62: Yes), the manufacturing line is determined to be normal, and the operation of the manufacturing line is continued (step S12). On the other hand, when a peak is not present in a range of equal to or higher than 1,000° C. and equal to or lower than 1,200° C., particularly, a range of equal to or higher than 1,100° C. and equal to or lower than 1,200° C. (step S62: No), it is determined that there is a high probability of the gate electrode GE manufactured in the manufacturing line being defective, and the manufacturing line is stopped. A manufacturing apparatus or process conditions are checked and corrected (step S64), and then the operation of the manufacturing line is restarted (step S12).

Figure 7:
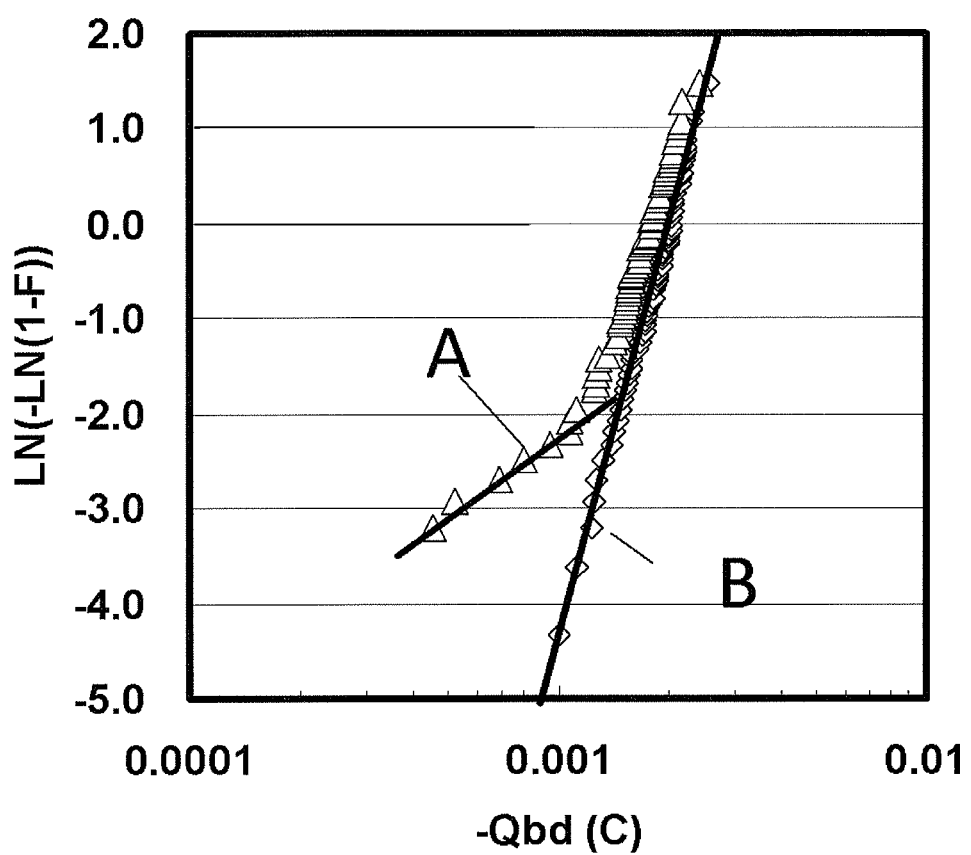
FIG. 7 is a diagram illustrating results obtained by measuring the dielectric breakdown lifetime of a gate insulating film GINS, in a Weibull distribution, when a MOS capacitive element is formed using the gate insulating film GINS and a gate electrode GE.

FIG. 7 shows results obtained by measuring the dielectric breakdown lifetime of the gate insulating film GINS, in a Weibull distribution, when a MOS capacitive element is formed using the gate insulating film GINS and the gate electrode GE. In the example shown in A, there are some samples which do not follow a straight line. In these samples, it is considered that since films having impurity barrier capability are not sufficiently formed on the surface of the gate electrode GE, impurities such as hydrogen pass through the gate electrode GE in a process of manufacturing a semiconductor device, enter the gate insulating film GINS, and reach an interface between the insulating film and the substrate, which leads to an extreme deterioration in the dielectric breakdown lifetime of the gate insulating film GINS.

On the other hand, in the example shown in B, almost all the samples follow a straight line. It is considered that this is because in almost all the samples, films having impurity barrier capability are sufficiently formed on the surface of the gate electrode GE.

Therefore, according to the present embodiment, it is possible to prevent a semiconductor device in which films having impurity barrier capability are not sufficiently formed on the surface of the gate electrode GE from being manufactured. Therefore, it is possible to prevent the dielectric breakdown lifetime of the gate insulating film GINS from being extremely lowered in the semiconductor device.

Third Embodiment

Figure 8A:
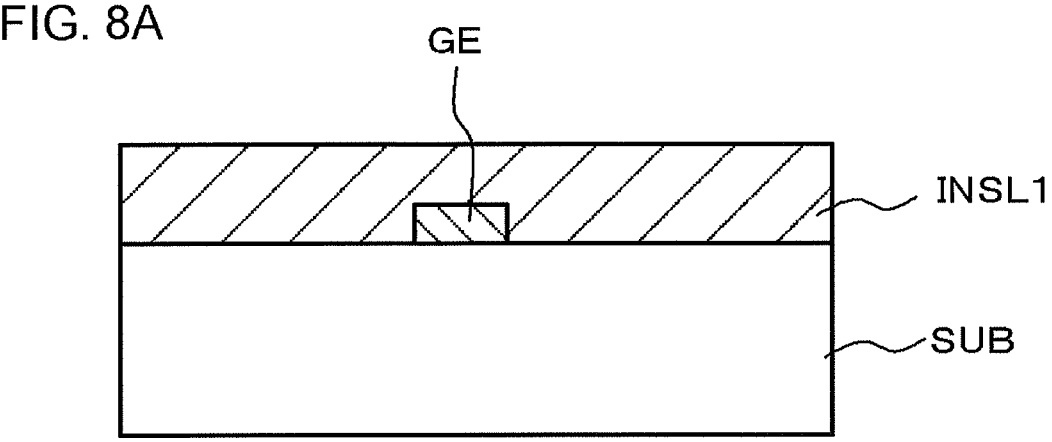
FIGS. 8A and 8B are cross-sectional views illustrating a method of manufacturing a semiconductor device according to a third embodiment.
Figure 8B:
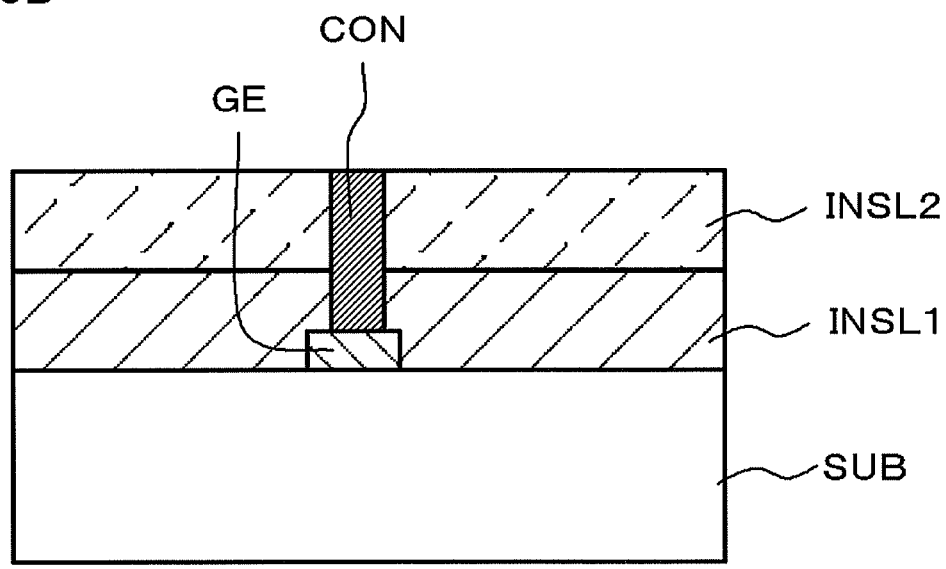

FIGS. 8A and 8B are cross-sectional views illustrating a method of manufacturing a semiconductor device according to a third embodiment. First, the substrate SUB is prepared. A semiconductor element is formed in the substrate SUB. The semiconductor element includes the well WEL, the element isolation film EI, the gate insulating film GINS, the gate electrode GE, the source SOU, and the drain DRN which are shown in, for example, the second embodiment. However, a semiconductor element having another structure may be formed in the substrate SUB. As shown in FIG. 8A, a first insulating film INSL1 is formed on the substrate SUB. The first insulating film INSL1 is, for example, a phosphorus doped silicate glass (PSG) film. Thereafter, the first insulating film INSL1 is etched back using plasma, and the thickness thereof is reduced.

Next, as shown in FIG. 8B, a second insulating film INSL2 is formed on the first insulating film INSL1. The second insulating film INSL2 is, for example, a $SiO_2$ film. The first insulating film INSL1 and the second insulating film INSL2 form, for example, one insulating interlayer. Thereafter, a plurality of contacts CON are buried in this insulating interlayer.

In the present embodiment, the processes shown in FIG. 6 are performed using the substrate SUB in a state shown in FIG. 8A as a sample. Here, the substance to be inspected in TDS is a substance (that is, SiO) having a mass of 44.

FIG. 9 is a diagram illustrating results of TDS in the present embodiment. In a sample shown in (a), no special processing is performed on the first insulating film INSL1 after film formation. On the other hand, in a sample shown in (b), the first insulating film INSL1 is etched back. In addition, in a sample shown in (c), the first insulating film INSL1 is etched back, and then is processed by APM (ammonia+hydrogen peroxide solution).

In the sample shown in (a), a peak (γ2) was seen in the vicinity of 1,200° C. On the other hand, in the samples shown in (b) and (c), the peak (γ2) was not seen. In addition, in the sample shown in (c), a peak (γ1) was seen in the vicinity of 1,050° C. instead of the peak (γ2). On the other hand, in the samples shown in (a) and (b), the peak (γ1) was not seen.

On the other hand, a withstand voltage between the contacts CON adjacent to the laminated film of the first insulating film INSL1 and the second insulating film INSL2 was measured with respect to each of the samples shown in (a), (b), and (c). A sufficient withstand voltage was obtained in the samples shown in (a) and (c), but a withstand voltage of the sample shown in (b) was relatively low. The reason for the occurrence of a difference between withstand voltages in this manner is considered as follows: since the surface of the sample shown in (b) does not have a base derived from high-temperature desorption peaks (γ1 and γ2), impurities infiltrate into the surface of the first insulating film INSL1 and react therewith. As a result, it is considered that binding between the surface of the first insulating film INSL1 and the interface of the second insulating film INSL2 weakens, and substances constituting the contact CON diffuse to this interface.

Therefore, according to the present embodiment, when the peaks (γ1 and γ2) of 1,000° C. or higher are not seen in TDS (step S62 of FIG. 6: No), a process shown in step S64 of FIG. 6 is performed, and thus it is possible to prevent the percent defective of a semiconductor device from being reduced due to a deterioration in the withstand voltage of the interface between the first insulating film INSL1 and the second insulating film INSL2.

As stated above, while the present invention devised by the inventors have been described specifically based on the embodiments thereof, the present invention is not limited to the above-mentioned embodiments, and it goes without saying that various changes and modifications may be made without departing from the scope of the invention.

It is apparent that the present invention is not limited to the above embodiment, and may be modified and changed without departing from the scope and spirit of the invention.

What is claimed is:

1. An inspection method comprising determining a quality of a product to be inspected including a substrate and a first film formed on the substrate by performing thermal desorption spectrometry (TDS) on the product to be inspected while raising a temperature of the product to 1,000° C. or higher, and checking for the presence or absence of a peak at 1,000° C. or higher.

2. The inspection method according to claim 1, wherein the first film is a silicon-containing film.

3. The inspection method according to claim 2, wherein the peak is located at 1,200° C. or lower.

4. The inspection method according to claim 2, wherein a second film is located between the first film and the substrate, the second film is a silicon oxide film or a silicon oxynitride film, and
the first film is a polysilicon film.

5. The inspection method according to claim 1, wherein the first film is formed using a CVD method.

6. The inspection method according to claim 1, further comprising determining that the quality of the product is normal in response to the peak at 1,000° C. or higher being expected and present.

7. The inspection method according to claim 1, further comprising determining that the quality of the product is defective in response to the peak at 1,000° C. or higher being expected and absent.

8. The inspection method according to claim 1, further comprising determining that the quality of the product is normal in response to the peak at 1,000° C. or higher being unexpected and absent.

9. The inspection method according to claim 1, further comprising determining that the quality of the product is defective in response to the peak at 1,000° C. or higher being unexpected and present.

10. The inspection method according to claim 1, wherein the checking for the presence or absence of the peak is performed at 1,100° C. or higher.

11. A method of manufacturing a semiconductor device, comprising:
a first film forming process of forming a first film over substrates; and
an inspection process of determining a quality of the first film by, after the first film forming process is performed on a first one of the substrates, performing TDS on the substrate while a processing temperature is raised to 1,000° C. or higher, and checking for the presence or absence of a peak at 1,000° C. or higher,
wherein when a height of the peak is equal to or greater than a reference in the inspection process, the first film forming process is performed on at least a second one of the substrates.

12. The method of manufacturing a semiconductor device according to claim 11, further comprising a second film forming process of forming a second film made of a silicon oxide film or a silicon oxynitride film before the first film forming process,
wherein the first film forming process is a process of forming a polysilicon film as the first film over the second film, using a CVD method,
the method further includes a patterning process of patterning at least the first film after the first film forming process,
in the inspection process, the presence or absence of the peak is checked for by performing TDS after the second film forming process and the first film forming process are performed on the first substrate, and before the patterning process is performed, and
when the height of the peak is equal to or less than a reference in the inspection process, the first film forming process, the second film forming process, and the patterning process are performed on at least a second one of the substrates.

13. The method of manufacturing a semiconductor device according to claim 12, wherein the second film is a tunnel insulating film or a gate insulating film, and the first film is a gate electrode.

14. The method of manufacturing a semiconductor device according to claim 12, wherein the peak is located at equal to or higher than 1,100° C. and equal to or lower than 1,200° C.

15. The method of manufacturing a semiconductor device according to claim 11, further comprising determining that the quality of the product is normal in response to the peak at 1,000° C. or higher being expected and present.

16. The method of manufacturing a semiconductor device according to claim 11, further comprising determining that the quality of the product is defective in response to the peak at 1,000° C. or higher being expected and absent.

17. The method of manufacturing a semiconductor device according to claim 11, further comprising determining that the quality of the product is normal in response to the peak at 1,000° C. or higher being unexpected and absent.

18. The method of manufacturing a semiconductor device according to claim 11, further comprising determining that the quality of the product is defective in response to the peak at 1,000° C. or higher being unexpected and present.

19. The method of manufacturing a semiconductor device according to claim 11, wherein the checking for the presence or absence of the peak is performed at 1,100° C. or higher.

* * * * *